(12) United States Patent
Miller

(10) Patent No.: US 6,210,335 B1
(45) Date of Patent: Apr. 3, 2001

(54) ACOUSTIC FLASH TO INCREASE PENETRATION

(75) Inventor: Steven C. Miller, Waukesha, WI (US)

(73) Assignee: General Electric Company, Milwaukee, WI (US)

(*) Notice: Subject to any disclaimer, the term of this patent is extended or adjusted under 35 U.S.C. 154(b) by 0 days.

(21) Appl. No.: 09/456,859

(22) Filed: Dec. 8, 1999

(51) Int. Cl.[7] .................................................. A61B 8/00
(52) U.S. Cl. ................................... 600/454; 600/451
(58) Field of Search ................................. 600/443, 454, 600/447, 449, 451, 455, 453, 437

(56) References Cited

U.S. PATENT DOCUMENTS

| | | | |
|---|---|---|---|
| 5,443,071 | * 8/1995 | Banjanin et al. | 600/451 |
| 5,694,937 | * 12/1997 | Kamiyama | 600/447 |
| 5,860,928 | * 1/1999 | Wong et al. | 600/453 |
| 6,048,312 | * 4/2000 | Ishrak et al. | 600/443 |

* cited by examiner

Primary Examiner—Marvin M. Lateef
Assistant Examiner—Maulin Patel
(74) Attorney, Agent, or Firm—McAndrews, Held&Malloy; Christian G. Cabou; Phyllis Y. Price

(57) ABSTRACT

Upon detection of systole by a detector (21), a master controller (20) adjusts a transmit level control (36) to cause a transducer array (2) to transmit ultrasound waves with a high acoustic output approaching the mechanical index FDA limit with sufficient dwell time between HAO frames to limit the temporal average below the FDA limit. The dwell time may be occupied by lower acoustic output frames (LAO) which are generated using the transmit level control (36).

18 Claims, 3 Drawing Sheets

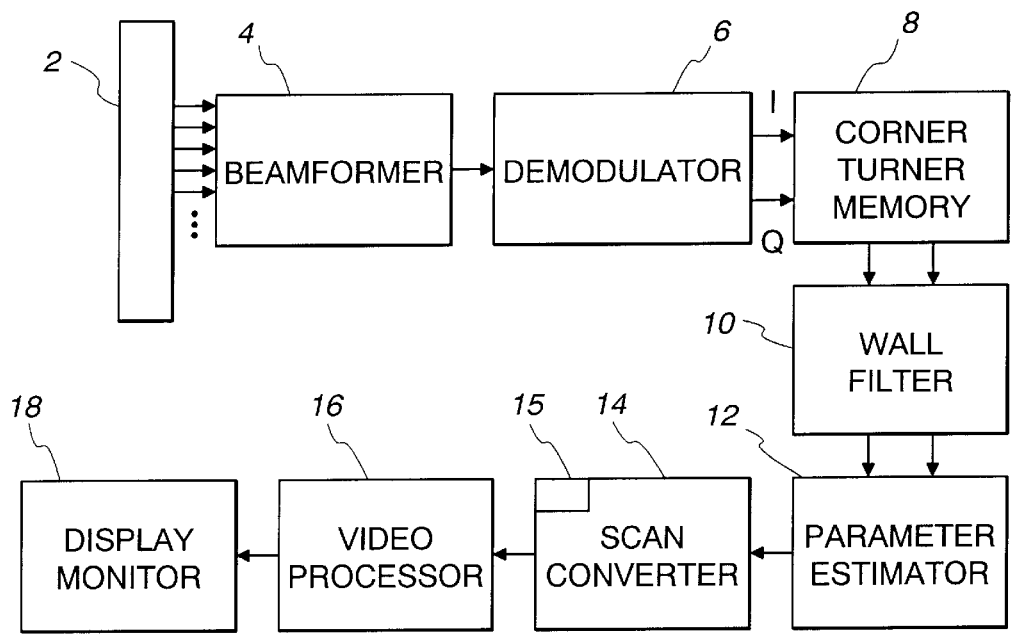
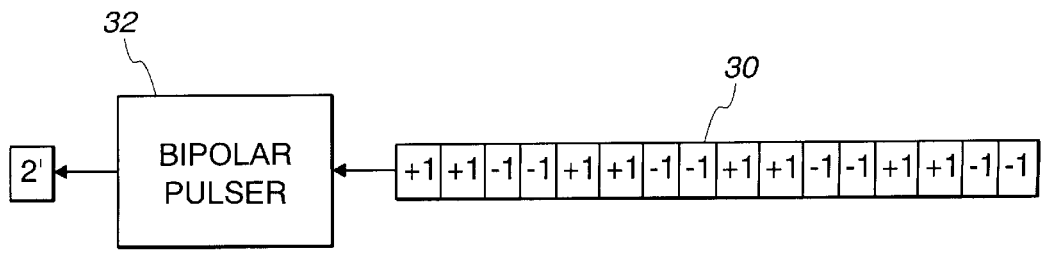

ACOUSTIC FLASH TO INCREASE PENETRATION

BACKGROUND OF THE INVENTION

This invention generally relates to ultrasound imaging, and more particularly relates to penetration of ultrasound waves into a subject being imaged.

The ultrasound wave penetration of current day diagnostic ultrasound machines when performing color flow imaging is compromised by FDA regulation. The FDA regulates the acoustic power output from diagnostic ultrasound imaging machines to avoid the possibility of undesirable effects in the body due to cavitation and heating. These effects are regulated by means of limits on MI (Mechanical Index), and ISPTA (Intensity Spatial Peak Temporal (time) Average), respectively. Ultrasound waves typically are applied to a subject by holding the face of a transducer against the skin of the subject. The temperature of the transducer face is limited for safety. When performing color flow imaging, an ultrasound imaging system typically reaches the ISPTA and probe temperature limits before reaching the MI limits. As a result, the system limits the transmit current to a level much lower than would be required to avoid the MI limit. The current limitation compromises the system's ability to image deep vessels where the limited transmit signal is highly attenuated.

A primary method used to improve penetration is to increase the number of firings (transmit & receive) in the same direction and perform some type of averaging across these firings. The primary disadvantage to this approach is the resulting decrease in the frame rate of the display, thereby degrading temporal resolution.

BRIEF SUMMARY OF THE INVENTION

The preferred embodiment is useful in an ultrasound imaging system for penetrating a subject (e.g., a human patient) with ultrasound waves and displaying a color flow image representing at least a portion of the subject. In such an environment, the preferred embodiment improves the penetration of the ultrasound waves while complying with mechanical index, temperature, and intensity spatial peak temporal average specifications. The improvement is provided by transmitting first ultrasound waves with a first power toward a portion of the subject in response to a first command, and receiving first reflected ultrasound waves from the subject in response to the first ultrasound waves. Second ultrasound waves with a second power less than the first power also are transmitted toward the portion of the subject in response to a second command, and second reflected ultrasound waves are received from the subject in response to the second ultrasound waves. The transmitting and receiving are preferably accomplished with a transducer array. A first set of signals is generated in response to the first reflected ultrasound waves and a second set of signals is generated in response to the second reflected ultrasound waves, preferably by an ultrasound receiver. The first command is generated for a first time period, and the second command is generated for a second time period, preferably by a processor. The ratio of the first time period to the second time period enables compliance with the mechanical index, temperature, and intensity spatial peak temporal average specifications, while enabling penetration of the ultrasound waves during the first time period. The first set of signals and second set of signals are processed to generate processed color flow data for display as a color flow image, preferably by a processor. A color flow image is displayed in response to the processed color flow data, preferably on a display monitor.

By using the foregoing techniques, the penetration of ultrasound waves into a subject being studied can be improved while still complying with applicable FDA regulation.

BRIEF DESCRIPTION OF THE DRAWINGS

FIG. 1 is a block diagram showing the signal processing chain for a conventional color flow ultrasound imaging system.

FIG. 3 is a block diagram depicting an exemplary transmit sequence for controlling a bipolar pulser connected to a transducer element.

DETAILED DESCRIPTION OF THE INVENTION

Figure 2:
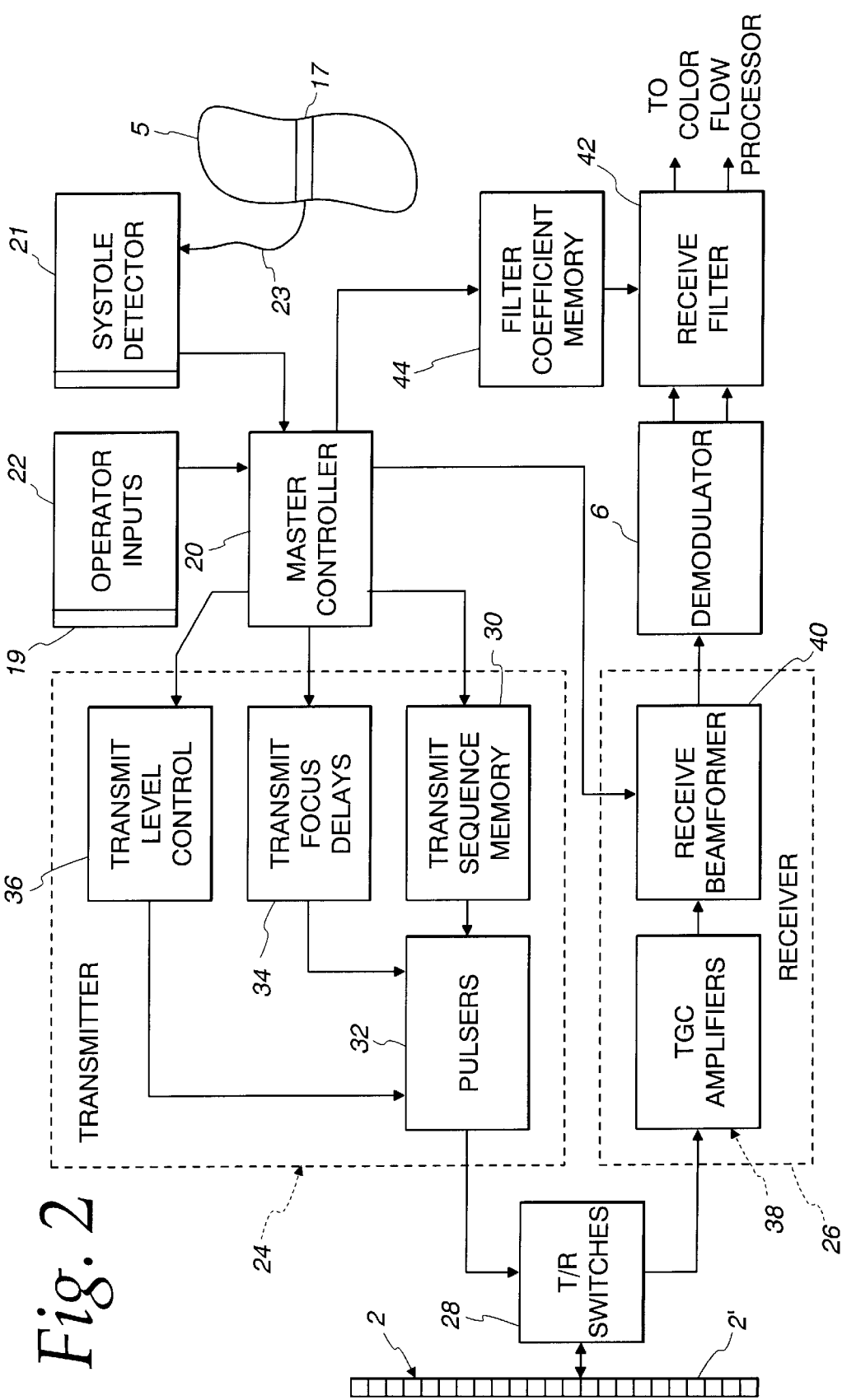
FIG. 2 is a block diagram showing the front end of a color flow ultrasound imaging system in accordance with a preferred embodiment of the invention.

Referring to FIG. 1, the basic signal processing chain for a color flow imaging system comprises an ultrasound transducer array 2, which is activated to transmit pulse sequences comprising tone bursts of ultrasound waves of length P which are fired repeatedly at the PRF. The return reflected RF ultrasound waves are detected by the transducer elements and received by the respective receive channels in the beamformer 4. The beamformer sums the delayed channel data and outputs a beamsummed signal, which is demodulated into in-phase and quadrature (I/Q) signal components by a demodulator 6. The I/Q signal components are stored in a corner turner memory 8, whose purpose is to buffer data from possibly interleaved firings and output the data as vectors of points across firings at a given range cell. Data is received in "fast time", or sequentially down range (along a vector) for each firing. The output of the corner turner memory is reordered into "slow time", or sequentially by firing for each range cell. The resultant "slow time" I/Q signal samples are passed through respective wall filters 10, which reject any clutter corresponding to stationary or very slow-moving tissue. The filtered outputs are then fed into a parameter estimator 12, which converts the range cell information into the intermediate autocorrelation parameters N, D and R(O). N and D are the numerator and denominator for the autocorrelation equation, as shown below:

$$N = \sum_{i=1}^{M-1} (I_i Q_{i+1} - I_{i+1} Q_i) \quad (2)$$

$$D = \sum_{i=1}^{M-1} (I_i I_{i+1} + Q_i Q_{i+1}) \quad (3)$$

where $I_i$ and $Q_i$ are the demodulated, basebanded input data for firing i, and M is the number of firings in the packet. R(O) is approximated as a finite sum over the number of firings in a packet, as follows:

$$R(O) = \sum_{i=1}^{M-1} \frac{(I_i^2 + Q_i^2 + I_{i+1}^2 + Q_{i+1}^2)}{2} \quad (4)$$

A processor converts N and D into a magnitude and phase for each range cell. The equations used are as follows:

$$\phi(R(T)) = \tan^{-1}\left[\frac{N}{D}\right] \quad (6)$$

The parameter estimator processes the magnitude and phase values into estimates of power, velocity and turbulence. The phase is used to calculate the mean Doppler frequency, which is proportional to the velocity as shown below; R(O) and |R(T)| (magnitude) are used to estimate the turbulence.

The mean Doppler frequency in hertz is obtained from the phase of N and D and the pulse repetition time T:

$$\overline{f} = \frac{1}{2\pi T}\tan^{-1}\left[\frac{N}{D}\right] = \frac{1}{2\pi T}(\phi(R(T))) \quad (7)$$

The mean velocity is calculated using the Doppler shift equation below. Since θ, the angle between the flow direction and the sampling direction, is not known, cos θ is assumed to be 1.0.

$$\overline{v} = \frac{\overline{f}}{f_o} \frac{c}{2\cos\theta} \quad (8)$$

Preferably, the parameter estimator does not calculate the mean Doppler frequency as an intermediate output, but calculates $\overline{v}$ directly from the phase output of the processor using a look-up table.

The turbulence may be calculated in the time domain as a second-order series expansion of the variance of the mean Doppler frequency. The time domain expression for turbulence involves calculating the zero-lag and one-lag autocorrelation functions, R(O) and R(T) respectively. The exact autocorrelation functions are approximated by finite sums over the known data in the number of firings in a packet:

$$\sigma^2 = \frac{2}{(2\pi T)^2}\left[1 - \frac{|R(T)|}{R(O)}\right] \quad (9)$$

The mean value signal θ (R(T)) is an estimate of the mean Doppler frequency shift of the flowing reflectors, which in turn is proportional to the mean blood flow velocity. The variance signal $\sigma^2$ indicates the frequency spread of the flow signal component of the baseband echo signal. This value is indicative of flow turbulence, since laminar flow has a very narrow range of velocities, while turbulent flow is a mixture of many velocities. To indicate the strength of the signal from the flowing reflectors, the signal R(O) indicates the amount of the returned power in the Doppler-shifted flow signal.

The color flow estimates are sent to a scan converter 14, which converts the color flow image data into X-Y format frames for video display and stores the frames in memory 15. The scan-converted frames are passed to a video processor 16, which basically maps the video data to a display color map for video display. The color flow image frames are then sent to the video monitor 18 for display. Typically, either velocity or power are displayed alone or velocity is displayed in conjunction with either power or turbulence. System control is centered in a host computer (not shown), which accepts operator inputs through an operator interface (e.g., a keyboard) and in turn controls the various subsystems.

The present invention may be incorporated in a system of the type depicted in FIG. 1 or other compatible color flow imaging systems. The preferred embodiment is shown in FIG. 2. System control is centered in a master controller or processor 20 (or host computer), which accepts operator inputs through an operator interface 22 and in turn controls the various subsystems. The master controller 20 also generates the system timing and control signals which are distributed via various control buses. The transducer array 2 consists of a plurality of separately driven transducer elements 2', each of which produces a burst of ultrasonic energy (i.e., ultrasound waves) when energized by a pulsed waveform produced by a transmitter 24. The ultrasonic energy (i.e., ultrasound waves) reflected back to transducer array 2 from the object under study is converted to an electrical signal by each receiving transducer element 2' and applied separately to a receiver 26 through a set of transmit/receive (T/R) switches 28. Transmitter 24 and receiver 26 are operated under control of master controller 20. A complete scan is performed by acquiring a series of echoes in which transmitter 24 is gated ON momentarily to energize each transducer element 2', and the subsequent echo signals produced by each transducer element 2' are applied to receiver 26. A channel may begin reception while another channel is still transmitting. The receiver 26 combines the separate echo signals from each transducer element to produce a single echo signal which is used to produce a line in an image on the display monitor.

In accordance with the preferred embodiment of the invention, adjustment of the length of the transmit pulses in each channel is implemented by programming a digital transmit sequence memory 30. Each transducer element 2' in the transmit aperture is pulsed by a pulse waveform output by a respective pulser 32 in response to a respective transmit sequence output to that pulser from the transmit sequence memory 30. The length of each pulse waveform (i.e., burst) is proportional to the number of bits in the respective digital transmit sequence. For example, FIG. 3 shows one such transmit sequence stored in transmit sequence memory 30 for driving a transducer element 2' with a burst of four cycles. In the case of bipolar pulsers, the +1 and −1 elements of each transmit sequence are transformed into pulses of opposite phase.

Under the direction of master controller 20, the transmitter 14 drives transducer array 2 such that the ultrasonic energy is transmitted as a directed focused beam. To accomplish focusing, respective time delays are imparted to the pulsers 32 by a transmit focus delay block 34, while respective peak pulse amplitudes are set by transmit level control block 36. The master controller 20 determines the conditions under which the acoustic pulses will be transmitted. With this information, the transmit focus delay and transmit level control blocks will respectively determine the timing and the amplitude of each of the transmit pulses to be generated by the pulsers 32. The pulsers 32 in turn send the transmit pulses to respective elements 2' of the transducer array 2 via the T/R switches 28, which protect the time-gain control (TGC) amplifiers 38 from the high voltages which may exist at the transducer array. By appropriately adjusting the transmit focus time delays in a conventional manner, an ultrasonic beam can be directed and focused at a transmit focal position.

The echo signals produced by each burst of ultrasonic energy reflect from objects located at successive ranges along each ultrasonic beam. Due to the differences in the propagation paths between a reflecting point and each transducer element, the echo signals will not be detected simultaneously and their amplitudes will not be equal. Receiver 26 amplifies the separate echo signals via a respective TGC amplifier 38 in each receive channel. The amplified echo signals are then fed to the receive beamformer 40, which imparts the proper time delays to the respective amplified echo signals. The receive time delays, like the transmit time delays, are provided under the control of the master controller. The receive time delays may be read out from look-up tables stored in random access memory. The receive beamformer 40 sums the time-delayed signals to provide an echo signal which accurately indicates the total ultrasonic energy reflected from a point located at a particular range along the ultrasonic beam.

The beamsummed receive signals are output to the demodulator 6, which forms the I and Q baseband components. These baseband components are bandpass-filtered in respective receive filters 42, which preferably take the form of finite impulse response filters. The filter coefficients are provided to the receive filters 42 from a filter coefficient memory 44 under the control of master controller 20. The bandwidth of the receive filters can be adjusted by changing the filter coefficients. The filtered outputs are then processed by the color flow processor, i.e., corner turner memory 8, wall filters 10 and a parameter estimator 12 shown in FIG. 1. As described above, the parameter estimator preferably includes a velocity estimator which estimates velocity as a function of the phase shift in the backscattered signals.

Figure 4:
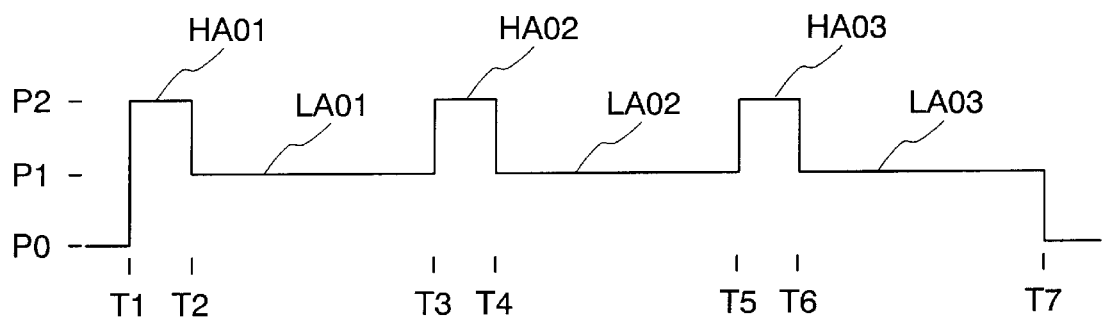
FIG. 4 is a timing diagram showing high acoustic frames separated by lower acoustic output frames.

Referring to FIG. 2, a subject being studied S is fitted with a conventional detector of heart activity 17 which transmits signals over a conductor 23 to a systole detector 21, such as a conventional ECG machine. Detector 21 detects systole of the heart of the subject and transmits a signal to master controller 20 that initiates a mode of operation illustrated in FIG. 4. The systole signal is received at time T1, and in response to the signal, the master controller causes transmit level control 36 to energize pulsars 32 so that transducer array 2 generates ultrasound waves with high acoustic output that result in several frames of high acoustic output (HAO) between times T1 and T2. The HAO is indicated by power level P2 in FIG. 4. The HAO approaches the MI (mechanical index) FDA limit with a sufficient dwell time between the HAO frames to limit the temporal average to below the FDA limit. One such dwell time, as shown in FIG. 4, is from time T2 to time T3, during which master controller 20 causes transmit level control 36 to energize pulsars 32 so that transducer array 2 transmits ultrasound waves into subject S at a lower acoustic power (LAO) illustrated by power level P1 in FIG. 4. The power level P0 in FIG. 4 indicates no scanning of the subject, i.e., no transmission of ultrasound waves by transducer array 2.

As shown in FIG. 4, the foregoing mode of operation results in HAO frames interspersed with LAO frames. More specifically, HAO frames HAO1 and HA02 are separated by LAO frames LAO1. Likewise, HAO frames HAO2 and HAO3 are separated by LAO frames LAO2. In addition, a series of LAO frames designated LAO3 in FIG. 4 follow HAO frames HAO3. The HAO1 frames are generated between times T1 and T2; the LAO1 frames are generated between times T2 and T3; the HAO2 frames are generated between times T3 and T4; the LAO2 frames are generated between times T4 and T5; the HAO3 frames are generated between times T5 and T6 and the LAO3 frames are generated between times T6 and T7. As illustrated in FIG. 4, the HAO frames are generated during a substantially smaller time period then the LAO frames. For real time imaging, the HAO frames are inserted sparsely between many LAO frames to limit the ISPTA over a time interval greater than a single frame but less than the thermal time constant of tissue. The preferred approach is to trigger one or more of the HAO frames at systole, when flow from the heart of a subject S is greatest in the region of interest, with several LAO frames in between. For example, referring to FIG. 4, systole occurs at times T1, T3 and T5, thereby initiating generating of HAO frames, HAO1, HAO2 and HAO3, respectively. The HAO frames are used to discriminate between image regions with flow and those without flow. Where no flow is present in an HAO frame, no flow is allowed in display 18. The regions of the HAO frames with flow are updated by flow estimates in the LAO frames to maintain good temporal resolution, i.e., frame rate, all providing better penetration and flow segmentation.

Referring to FIG. 4, an exemplary time period for generating frames HAO1 is approximately 200 milliseconds. An exemplary time period for generating frames LAO1 is approximately 800 milliseconds. As shown in FIG. 4, the time periods for generating each of the HAO frames may be identical; the time periods for generating each of the LAO frames also may be identical.

Figure 5:
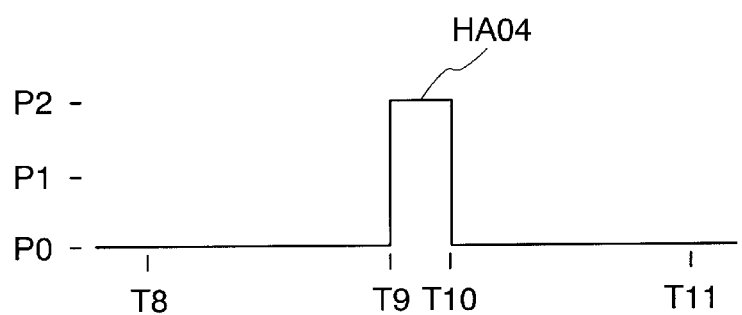
FIG. 5 is a timing diagram showing high acoustic output frames used in a flash freeze mode operation.
Figure 6:
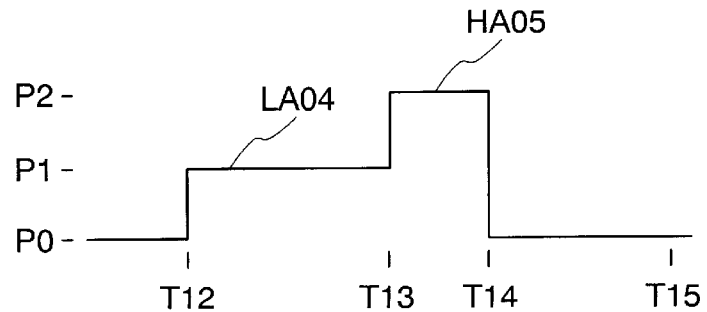
FIG. 6 is a timing diagram showing lower acoustic output frames and high acoustic output frames used in a flash freeze mode of operation.

FIGS. 5 and 6 illustrate two different techniques for generating still (frozen) images. According to these techniques, a user pushes a "flash-freeze" key 19 on operator inputs 22 (FIG. 2). The system responds in three steps:

1. Assuming key 19 is pushed at time T8, the system briefly pauses scanning between times T8 and T9;
2. Fires a small number of HAO frames, HAO4, between times T9 and T10; and 3. Pauses scanning from time T10 until the user pushes key 19 again at time T11.

Referring to FIG. 6, a still frozen image may be obtained by having the user press key 19 (FIG. 2) to which the system also responds in three steps:

1. Assuming the user pushes key 19 at time T12, the system fires a small number of LAO frames between times T12 and T13;
2. Fires a small number of HAO frames, HAO5, between times T13 and T14; and
3. Pauses scanning after time T14 until the user again pushes key 19 at time T15.

The system pauses a minimum time to insure that the ISPTA is not exceeded. This approach provides a frozen image with increased penetration on display 18.

Those skilled in the art will recognize that other parameters should be adjusted in addition to the transmit current for the HAO frames, including system gain and segmentation thresholds.

The foregoing preferred embodiments have been disclosed for the purpose of illustration. Variations and modifications of the embodiments will be readily apparent to persons skilled in the art. All such variations and modifications are intended to be encompassed by the claims set forth hereinafter. For example, controller 20 may comprise a microprocessor or digital signal processor or other types of logic units capable of executing logical or arithmetic operations.

What is claimed is:

1. In an ultrasound imaging system for penetrating a subject being studied with ultrasound waves and displaying a color flow image representing at least a portion of the subject, apparatus for improving the penetration of the ultrasound waves while complying with mechanical index, temperature and intensity spatial peak temporal average specifications comprising in combination:

a transducer array operable in response to a first command for transmitting ultrasound waves with a first power toward a portion of the subject and receiving first reflected ultrasound waves from the portion and operable in response to a second command for transmitting ultrasound waves with a second power less than the first power toward the portion of the subject and receiving second reflected ultrasound waves from the portion;

an ultrasound receiver connected to generate a first set of signals in response to the first reflected ultrasound waves and connected to generate a second set of signals in response to the second reflected ultrasound waves;

a processor generating the first command for a first time period and generating the second command for a second time period, the ratio of the first time period to the second time period enabling compliance with said mechanical index, temperature and intensity spatial peak temporal average specifications while enabling penetration of said ultrasound waves during the first time period, and processing the first set of signals and the second set of signals to generate processed color flow data for display as a color flow image; and a display displaying a color flow image in response to said processed color flow data.

2. Apparatus, as claimed in claim 1, wherein the first time period is sufficient to generate a frame of said first scan data.

3. Apparatus, as claimed in claim 1, wherein the first power approaches the mechanical index specification and wherein said first command comprises a series of first commands with sufficient dwell time between the first commands to comply with said mechanical index, temperature and intensity spatial peak temporal average specifications.

4. Apparatus, as claimed in claim 1, wherein the subject being studied has a heart exhibiting systole and wherein said processor generates said first command in response to said systole.

5. Apparatus, as claimed in claim 1, wherein said processor identifies flow data within the first scan data representing a region of fluid flow within the portion of the subject.

6. Apparatus, as claimed in claim 5, wherein said processor prevents the display of said color flow image in the event flow data is not identified within the first scan data.

7. Apparatus, as claimed in claim 1, wherein said first time period is a predetermined time period, wherein said second time period is a predetermined time period, and wherein said processor enables the display of still color images by generating said second command for said predetermined second time period and generating said first command for said predetermined first time period.

8. Apparatus, as claimed in claim 7, wherein said predetermined first time period is sufficient to generate a plurality of frames of said first set of signals and wherein said predetermined second time period is sufficient to generate a plurality of frames of said second set of signals.

9. Apparatus, as claimed in claim 7, and further comprising an input generating a freeze signal in response to operation by a user and wherein said processor generates said first and second commands in response to said freeze signal.

10. In an ultrasound imaging system for penetrating a subject being studied with ultrasound waves and displaying a color flow image representing at least a portion of the subject, a method of improving the penetration of the ultrasound waves while complying with mechanical index, temperature and intensity spatial peak temporal average specifications comprising in combination:

transmitting first ultrasound waves with a first power toward a portion of the subject in response to a first command;

receiving first reflected ultrasound waves from the portion in response to the first ultrasound waves;

transmitting second ultrasound waves with a second power less than the first power toward the portion of the subject in response to a second command;

receiving second reflected ultrasound waves from the portion in response to the second ultrasound waves;

generating a first set of signals in response to the first reflected ultrasound waves;

generating a second set of signals in response to the second reflected ultrasound waves;

generating the first command for a first time period;

generating the second command for a second time period, the ratio of the first time period to the second time period enabling compliance with said mechanical index, temperature and intensity spatial peak temporal average specifications while enabling penetration of said ultrasound waves during the first time period;

processing the first set of signals and the second set of signals to generate processed color flow data for display as a color flow image; and displaying a color flow image in response to said processed color flow data.

11. A method, as claimed in claim 10, wherein the first time period is sufficient to generate a frame of said first set of signals.

12. A method, as claimed in claim 10, wherein the first power approaches the mechanical index specification and wherein said first command comprises a series of first commands with sufficient dwell time between the first commands to comply with said mechanical index, temperature and intensity spatial peak temporal average specifications.

13. A method, as claimed in claim 10, wherein the subject being studied has a heart exhibiting systole and wherein said first command is generated in response to said systole.

14. A method, as claimed in claim 10, and further comprising identifying flow data within the first set of signals representing a region of fluid flow within the portion of the subject.

15. A method, as claimed in claim 14, wherein said displaying comprises preventing the display of said color flow image in the event flow data is not identified within the first set of signals.

16. A method, as claimed in claim 10, wherein said first time period is a predetermined time period, wherein said second time period is a predetermined time period, and wherein said displaying comprises displaying a still color image by generating said second command for said predetermined second time period and generating said first command for said predetermined first time period.

17. A method, as claimed in claim 16, wherein said predetermined first time period is sufficient to generate a plurality of frames of said first set of signals and wherein said predetermined second time period is sufficient to generate a plurality of frames of said second set of signals.

18. A method, as claimed in claim 16, and further comprising generating a freeze signal in response to operation by a user and wherein said first and second commands are generated in response to said freeze signal.

* * * * *